United States Patent [19]
Knott

[11] Patent Number: 5,690,620
[45] Date of Patent: Nov. 25, 1997

[54] ANATOMICALLY CONFORMING NASOGASTRIC TUBE WITH NORMALLY-CURVED TIP AND METHOD FOR USING SAME

[76] Inventor: Michael McFarland Knott, P.O. Box 5577, Tahoe City, Calif. 96145

[21] Appl. No.: 697,104

[22] Filed: Aug. 19, 1996

[51] Int. Cl.$^6$ ............................................. A61M 25/00
[52] U.S. Cl. ............................................. 604/280; 604/281
[58] Field of Search ............................................. 604/34, 174, 280, 604/282, 49, 251, 264, 281

[56] References Cited

U.S. PATENT DOCUMENTS

| | | |
|---|---|---|
| 686,281 | 11/1901 | Gerry . |
| 883,583 | 3/1908 | Stallsmith . |
| 1,060,665 | 5/1913 | Bell . |
| 1,596,754 | 8/1926 | Moschelle . |
| 2,685,289 | 8/1954 | Devine . |
| 3,042,045 | 7/1962 | Sheridan . |
| 3,058,472 | 10/1962 | Thornton . |
| 3,094,124 | 6/1963 | Birtwell ............................................. 604/280 |
| 3,153,415 | 10/1964 | Sheridan . |
| 3,155,097 | 11/1964 | Barron . |

(List continued on next page.)

Primary Examiner—Sam Rimell
Attorney, Agent, or Firm—Skjerven, Morrill, MacPherson, Franklin, & Friel, LLP; Patrick T. Bever

[57] ABSTRACT

A nasogastric (NG) tube provided with a normally-curved or normally-bent leading end. When passed, the normally-curved/bent leading end negotiates the nasopharynx with the tip of the NG tube biased to conform to the shape of the soft palate, thereby applying a reduced pressure against the posterior nasopharynx. After passing the nasopharynx, the normally-curved/bent leading end is rotated 180° such that the tip is biased in a posterior direction such that it more reliably enters the esophagus. After entering the esophagus, the NG tube is rotated an additional 90° such that when the tip of the NG tube enters the stomach, the tip is biased toward the stomach outlet. A second curved portion located near the normally-curved/bent leading end provides additional biasing force to help the tip enter the esophagus. A longitudinal line, stripe or other form of marking is placed on the tube to prompt the nurse/physician when to make the 180° and 90° rotations.

15 Claims, 8 Drawing Sheets

U.S. PATENT DOCUMENTS

| | | | |
|---|---|---|---|
| 3,395,710 | 8/1968 | Stratton et al. | |
| 3,430,631 | 3/1969 | Abramson | |
| 3,508,554 | 4/1970 | Sheridan | 604/280 |
| 4,059,111 | 11/1977 | Erasmus | 604/54 |
| 4,168,703 | 9/1979 | Kenigsberg | |
| 4,180,076 | 12/1979 | Betancourt | |
| 4,182,342 | 1/1980 | Smith | |
| 4,270,542 | 6/1981 | Plumley | |
| 4,275,724 | 6/1981 | Behrstock | |
| 4,307,719 | 12/1981 | McParland | |
| 4,318,402 | 3/1982 | Vaillancourt | |
| 4,327,720 | 5/1982 | Bronson et al. | |
| 4,363,323 | 12/1982 | Geiss | |
| 4,402,684 | 9/1983 | Jessup | 604/264 |
| 4,485,805 | 12/1984 | Foster, Jr. | |
| 4,543,089 | 9/1985 | Moss | 604/93 |
| 4,547,192 | 10/1985 | Brodsky et al. | 604/270 |
| 4,613,323 | 9/1986 | Norton et al. | 604/43 |
| 4,622,034 | 11/1986 | Shattuck | 604/179 |
| 4,631,054 | 12/1986 | Kim | 604/54 |
| 4,634,425 | 1/1987 | Meer | 604/54 |
| 4,687,470 | 8/1987 | Okada | 604/171 |
| 4,705,709 | 11/1987 | Vailancourt | 428/36 |
| 4,747,827 | 5/1988 | Micek | 604/54 |
| 4,747,840 | 5/1988 | Ladika et al. | 604/281 |
| 4,778,448 | 10/1988 | Meer | 604/54 |
| 4,781,704 | 11/1988 | Potter | 604/270 |
| 4,784,638 | 11/1988 | Ghajar et al. | 604/280 X |
| 4,790,832 | 12/1988 | Lopez | 604/283 |
| 4,795,442 | 1/1989 | Traflet | 604/179 |
| 4,801,294 | 1/1989 | Okada | 604/171 |
| 4,828,550 | 5/1989 | Kurimoto | 604/171 |
| 4,838,879 | 6/1989 | Tanabe et al. | 604/280 |
| 4,874,365 | 10/1989 | Frederick et al. | 604/54 |
| 4,878,762 | 11/1989 | Uddo, Jr. et al. | 383/33 |
| 4,884,573 | 12/1989 | Wijay et al. | 604/282 X |
| 4,886,506 | 12/1989 | Lougren et al. | 604/282 X |
| 4,887,997 | 12/1989 | Okada | 604/54 |
| 4,895,562 | 1/1990 | Lopez | 604/48 |
| 4,955,375 | 9/1990 | Martinez | 128/207.15 |
| 4,986,815 | 1/1991 | Schneider | 604/180 |
| 4,998,919 | 3/1991 | Schnepp-Pesch et al. | 604/164 |
| 5,017,193 | 5/1991 | Fields | 604/270 |
| 5,037,387 | 8/1991 | Quinn et al. | 604/51 |
| 5,045,072 | 9/1991 | Castillo et al. | 604/280 |
| 5,057,091 | 10/1991 | Andersen | 604/270 |
| 5,057,093 | 10/1991 | Clegg et al. | 604/283 |
| 5,078,701 | 1/1992 | Grassi et al. | 604/54 X |
| 5,092,847 | 3/1992 | Pozzo | 604/170 |
| 5,147,315 | 9/1992 | Weber | 604/282 X |
| 5,152,756 | 10/1992 | Quinn et al. | 604/270 |
| 5,185,005 | 2/1993 | Ballantyne | 604/174 |
| 5,228,728 | 7/1993 | McNaughton et al. | 285/319 |
| 5,242,429 | 9/1993 | Nwaneri et al. | 604/270 |
| 5,318,530 | 6/1994 | Nelson, Jr. | 604/96 |
| 5,322,509 | 6/1994 | Rickerd | 604/280 X |
| 5,334,167 | 8/1994 | Cocanower | 604/280 |
| 5,360,414 | 11/1994 | Yarger | 604/264 |
| 5,380,276 | 1/1995 | Miller et al. | 604/28 |
| 5,401,241 | 3/1995 | Delany | 604/43 |
| 5,431,637 | 7/1995 | Okada et al. | 604/264 |
| 5,454,881 | 10/1995 | Fischer | 148/241 |
| 5,509,909 | 4/1996 | Moy | 604/281 |
| 5,549,581 | 8/1996 | Lurie et al. | 604/282 |

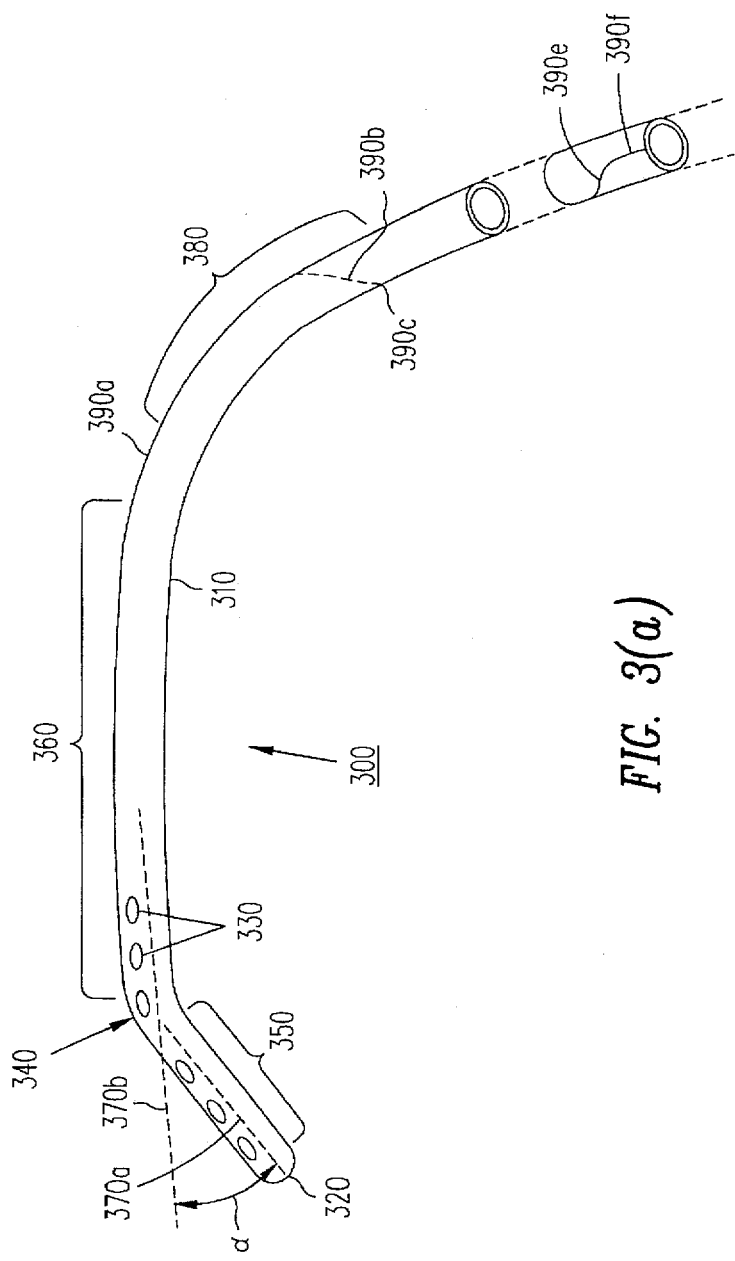
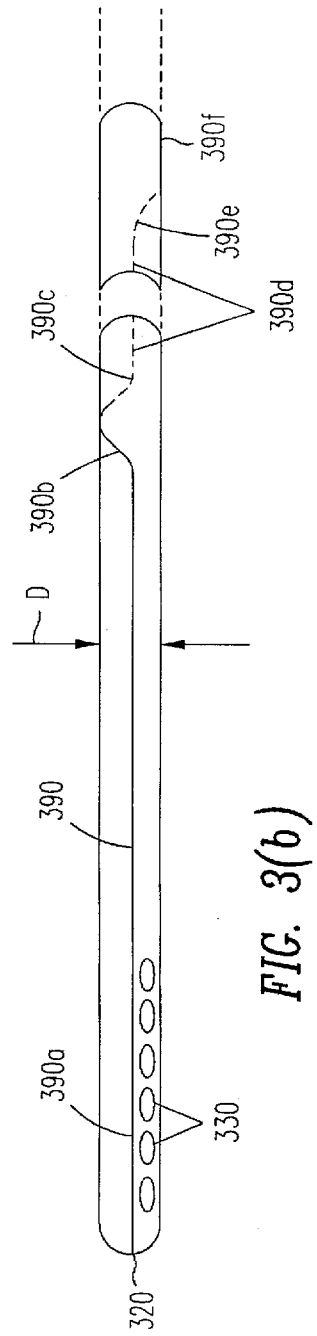
FIG. 3(a)
FIG. 3(b)

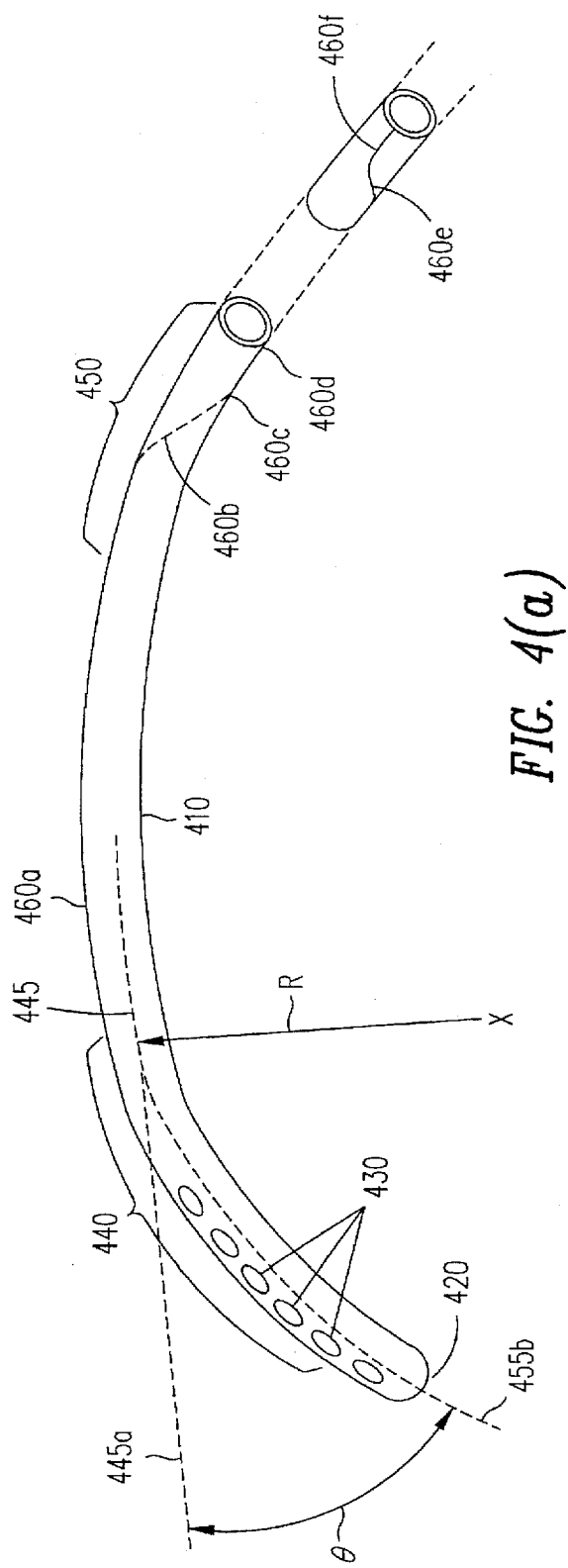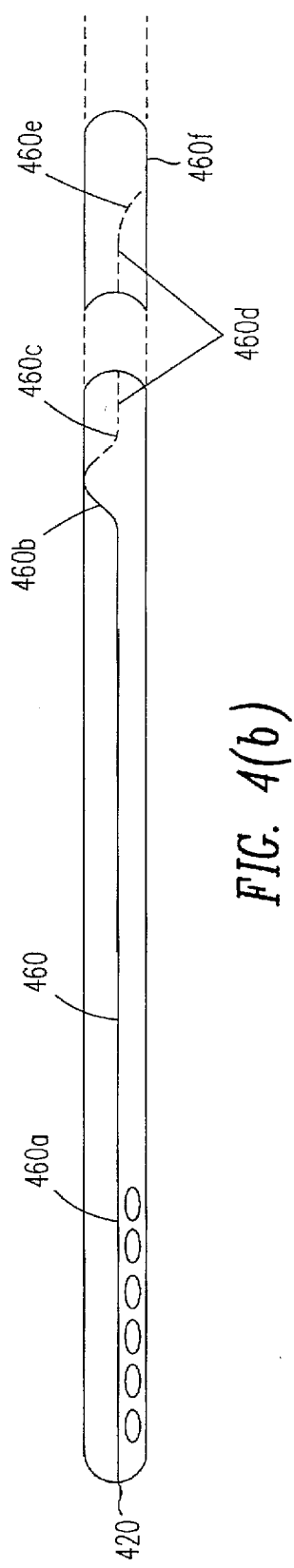

ANATOMICALLY CONFORMING NASOGASTRIC TUBE WITH NORMALLY-CURVED TIP AND METHOD FOR USING SAME

RELATED APPLICATION

This application claims priority of provisional application Ser. No. 60/017,590, filed May 14, 1996.

RELATED DISCLOSURE DOCUMENT

Reference is made to Disclosure Document No. 385088 which was filed in the U.S. Patent and Trademark Office on Oct. 31, 1995.

BACKGROUND OF THE INVENTION

1. Field of the Invention

The present invention pertains to nasogastric tubes which are tubes passed through the nose into the stomach.

2. Description of the Prior Art

A nasogastric (NG) tube is passed through a patient's nose, pharynx and esophagus into the stomach. The tubes provide a conduit through which liquids or gases may be removed from or instilled into the patient's stomach. NG tubes are typically used in hospitals to remove ingested poisons, pre-operatively to insure the stomach is empty, post-operatively to remove gas, and to treat bowel obstruction and blockage. NG tubes are used for feeding tubes in hospitals and nursing homes to allow passage of liquid food supplements into the stomach.

FIG. 1 shows a known NG tube 100 which is typically formed from a 3 to 4 foot length of stiff (but not rigid) plastic tubing 110 having a diameter D of 2 to 10 mm, depending on the type of use and the patient's size. One end of the tubing 110 is tapered and rounded to form a tip 120. In addition, the tubing 110 defines several openings 130 located near the tip 120 through which liquids or gases may enter or leave one or more passages formed within the tubing 110.

When packaged for shipment, NG tubes are typically wrapped in approximately 6 to 8 inch oval loops and include an initial straight portion 140 (approximately 4 to 6 inches long) which extends from the leading tip 120 to the beginning of the first packaging bend 150. As discussed below, the straight portion 140 and first packaging bend 150 are two design aspects which prevent easy passage of the NG tube.

FIGS. 2(a) through 2(d) show a procedure for passing the known NG tube shown in FIG. 1.

As shown in FIG. 2(a), the tip 120 of the NG tube is typically lubricated and then placed in one of the patient's nostrils 210 and pushed straight back through the nasal passage 220 until the leading tip 120 impacts the pharyngeal recess of the posterior nasopharynx 230 in a substantially perpendicular manner. At this point, the NG tube must be pushed against the posterior nasopharynx 230 to cause the initial straight portion of the tube to deform and deflect the tip 120 inferiorly toward the oropharynx 240. The pressure applied to the nasopharynx 230 during this process is dependent upon the stiffness of the NG tube and the amount of friction between the tip 120 and the nasopharynx 230. The pressure applied by the tip 120 against the posterior nasopharynx is particularly uncomfortable to patients, causing pain, gagging, coughing and frequently vomiting. In addition, this process can be dangerous in that, in the case of head-injured patients, the NG tube can inadvertently pass through the sphenoid bone (which lies behind the nasopharynx) and enter the brain.

Referring now to FIGS. 2(a) and 2(b), once the leading tip 120 has negotiated the bend from the nasal passage 220 into the oropharynx 240, the first packaging bend 150 has advanced into the patient's nasal passage 220. Typically, in present practice the packaging bend 150 is inserted with the concave portion of the bend facing downward (in the direction of arrow A). As the packaging bend 150 enters the nasal passage, the packaging bend 150 produces an upward force (in the direction of arrow B) on the nasal passage 220, specifically the inferior aspect of the inferior concha, which tends to force the tip 120 forward (in the direction of arrow C). As the NG tube is advanced through the oropharynx 240 and into the laryngopharynx 250, the tip 120 encounters two openings: the esophagus 260 and the voice box (vocal chords) 270 which is the opening to the trachea and subsequently the lungs. Ideally, the tip 120 is biased into the esophagus 260. However, because of the straight portion 140 of the NG tube, the tip 120 is basically hanging down from the nasopharynx 230, and is further biased forward (in the direction of arrow C) by the packaging bend 150. At this time, the administering nurse/physician will often instruct the patient to take small sips of water while advancing the NG tube in an attempt to have the swallowing process aid in leading tip 120 into the esophagus 260. However, as shown in FIG. 2(c), because the leading tip 120 is directed in the forward direction, the leading tip 120 can enter the voice box 260 and, if not properly diagnosed by the administering nurse/physician, can possibly pass through the trachea into the lungs, thereby causing severe damage or complications. Entry of the tip 120 into the trachea typically produces profound coughing, indicating incorrect placement. In this event, the NG tube must be partially withdrawn and again advanced toward the esophagus 260. There have been instances where positioning has been incorrect and various liquids have been instilled into the lungs. This is a truly unfortunate occurrence, fortunately rare, but usually results in dire consequences.

As shown in FIG. 2(d), once the tip 120 enters the esophagus 260, the NG tube is then advanced into the stomach (not shown) and correct positioning in the stomach is tested in one or preferably two ways. The first is attaching a syringe to the end of the tube and injecting air through the tube while listening over the stomach. A distinctive gurgling sound is heard, verifying that the tip 120 is properly located in the stomach. The second way is to aspirate from the tube with a syringe, thus obtaining stomach contents, also verifying correct placement.

As described above, a problem with the currently-known and presently-used NG tubes is that they produce profound discomfort during insertion and are difficult to direct into the esophagus and properly position in the stomach.

U.S. Pat. No. 4,747,827 teaches a method wherein a wire is inserted into the end of an NG tube and then bent into a curved shape. The NG tube can then be partially inserted into a patient while maintaining a relatively high degree of comfort. The wire is then withdrawn before the tip of the NG tube enters the esophagus. However, this method is unnecessarily time-consuming, complex, and exposes the patient to extreme risk should the wire pierce the tube or exit one of the openings in the tube. Moreover, this method can create discomfort as the bend in the wire passes through the nasal passage. Further, because the wire is withdrawn before the NG tube enters the esophagus, similar problems to those mentioned above exist regarding inadvertent entry of the NG tube into the trachea, and the proper positioning of the NG tube in the stomach.

SUMMARY OF THE INVENTION

The present invention is directed to an improved nasogastric (NG) tube which is easily and reliably passed through the nasopharynx and into the esophagus and stomach of the patient, thereby affording maximum comfort and minimum risk to the patient.

The present invention is also directed to a method for inserting an NG tube which is designed to be more easily and reliably passed into a patient such that the tip of the NG tube negotiates the nasopharynx with reduced discomfort, more reliably enters the esophagus, and is more easily positioned in the stomach outlet, thereby providing greater comfort and reduced risk to the patient.

In accordance with a first aspect of the present invention, a nasogastric (NG) tube is provided with a normally-curved or normally-bent leading end. The normally-curved or normally-bent leading end facilitates comfortable passing of the NG tube through the nasopharynx of a patient because the tip of the NG tube is biased to conform to the shape of the soft palate thereby applying minimal pressure against the posterior wall of the nasopharynx. Further, the normally-curved or bent leading end facilitates easier and more reliable passage into the esophagus of the patient when the NG tube is rotated 180° such that the tip is biased in a posterior direction. Finally, the normally-curved/bent leading end facilitates more reliable positioning in the stomach by rotating the tube 90° after entering the esophagus such that when the tip of the NG tube enters the stomach, the tip is directed toward the stomach outlet.

In accordance with a second aspect of the present invention, a second curved portion is formed 1 to 3 inches behind the normally-curved/bent leading end. This curved portion facilitates entry of the tip into the esophagus by enhancing the biasing force which presses the tip in the posterior direction, thereby aligning the tip for more reliable insertion into the esophagus.

In accordance with a third aspect of the present invention, a marking system, such as a longitudinal line or stripe, is formed on an outer surface of the NG tube to provide the administering nurse/physician with visual prompts regarding the orientation of the NG tube during insertion. In particular, the longitudinal line or stripe includes a first section formed along a convex portion of the first normally-curved/bent leading end, thereby allowing the nurse/physician to maintain the proper orientation of the leading tip as it passes through the nasopharynx. In addition, the longitudinal line or stripe includes a second section extending around the tube which prompts the nurse/physician to rotate the tube 180°, thereby properly orienting the tip in the posterior direction such that the tip is directed into the esophagus. Finally, the longitudinal line or stripe includes an additional section which prompts the nurse/physician to rotate the tube 90° after entering the esophagus, thereby providing a proper orientation such that the tip is received in the outlet portion of the stomach.

In accordance with a fourth aspect of the present invention, a method for passing a nasogastric tube having a normally-curved/bent leading end includes the steps of inserting the nasogastric tube into a nostril of the patient such that a concave side of the normally-curved/bent leading end faces downward (inferior) relative to the patient's head, rotating the nasogastric tube after the tip enters the oropharynx such that the closed end is biased toward the patient's spine, and further inserting the tube such that the tip enters the patient's esophagus. The method alternatively includes an additional step wherein, after entering the esophagus, the tube is rotated 90° such that the tip is in a proper orientation for placement into the outlet portion of the stomach.

BRIEF DESCRIPTION OF THE DRAWINGS

These and other features, aspects and advantages of the present invention will become better understood with regard to the following description, appended claims, and accompanying drawings, where:

FIGS. 3(a) and 3(b) show side and top views of a nasogastric tube according to a first embodiment of the present invention;

FIGS. 4(a) and 4(b) show side and top views of a nasogastric tube according to a second embodiment of the present invention.

DESCRIPTION OF THE PREFERRED EMBODIMENT

In accordance with a first aspect of the present invention, an improved nasogastric (NG) tube is provided by forming a normally-curved/bent leading portion which facilitates easier negotiation of the bend formed by the nasal passage and pharynx, easier entry into the esophagus, and easier positioning into the outlet of the stomach of the patient. In accordance with a second aspect of the present invention, the NG tube includes a second normally-curved portion formed a few inches behind the normally-curved/bent leading portion which further facilitates easier negotiation of the bend formed by the nasopharynx. In accordance with a third aspect of the present invention, markings, such as a longitudinal line or stripe, are provided on an outer surface of the NG tube to direct an administering nurse/physician regarding the proper orientation and rotation of the NG tube during insertion.

Figure 1:
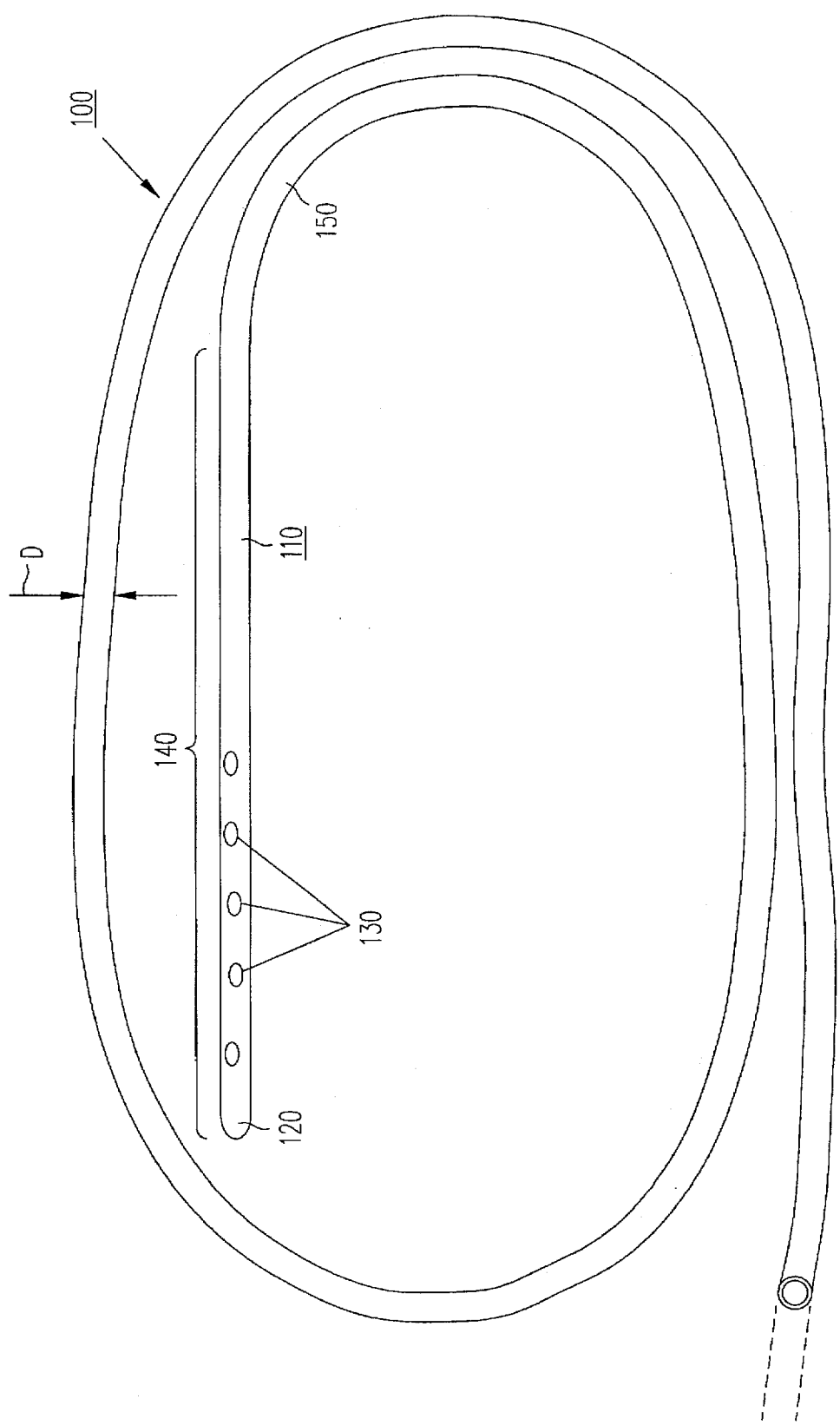
FIG. 1 is a side view showing a known nasogastric tube.
Figure 2A:
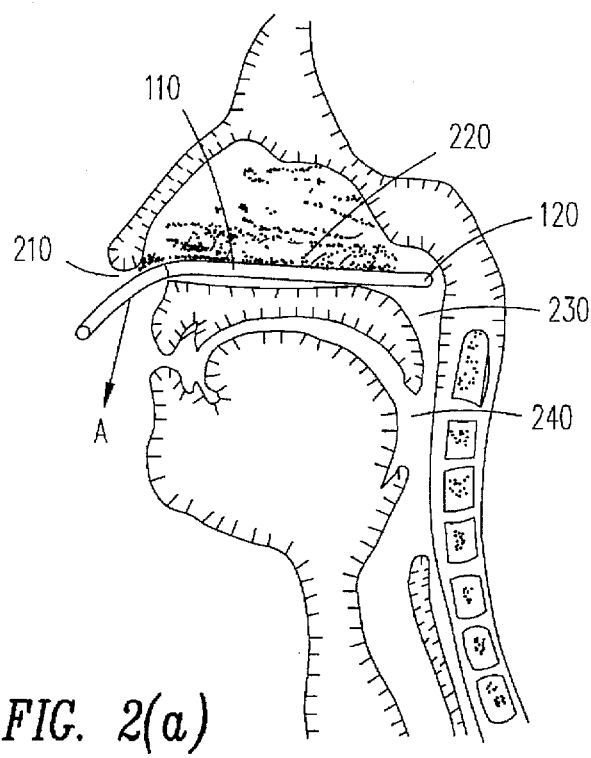
FIGS. 2(a) through 2(d) show procedural steps by which the known nasogastric tube is passed into a patient.
Figure 2B:
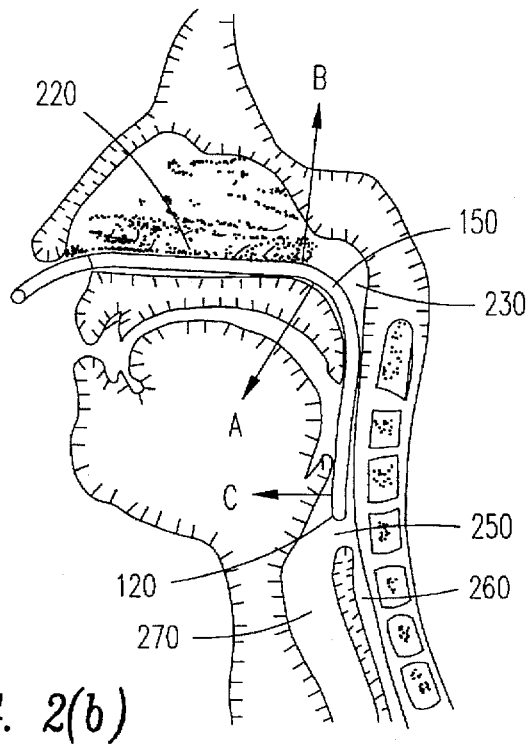
Figure 2C:
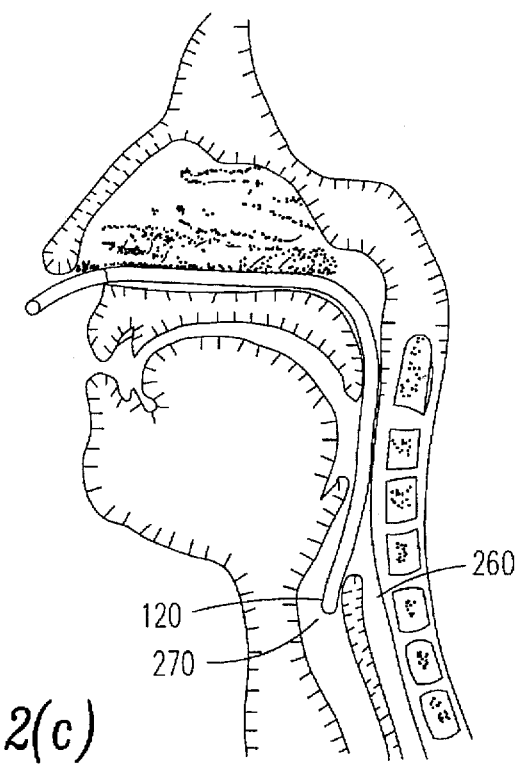
Figure 2D:
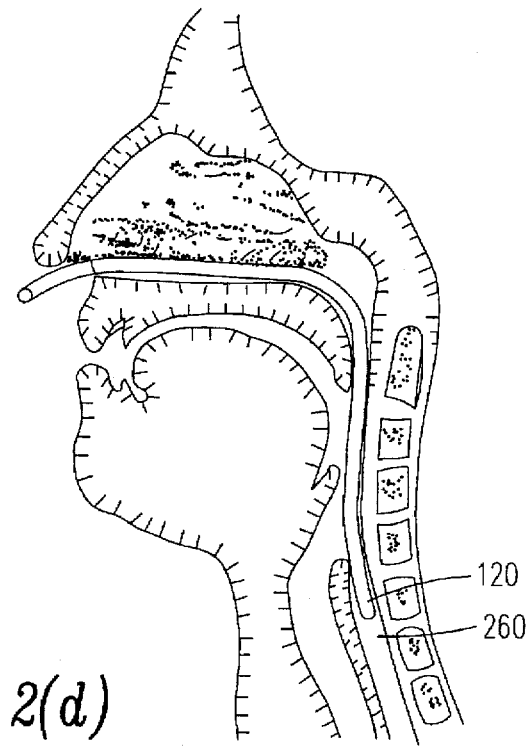

Other than the above-mentioned first, second and third aspects (which are described below in greater detail), the NG tube according to the present invention is essentially identical to known NG tubes, such as those shown in FIG. 1. In particular, the tubing material, diameters and lengths of the NG tube according to the present invention is essentially the same as those of known NG tubes.

As used herein, the terms "normally-curved" and "normally-bent" describe the degree of flexibility and resilience exhibited in known NG tubes. Those experienced with NG tubes will recognize that the curves and bends of known NG tubes (for example, the packaging bends 150 of the known NG tube 100, discussed above) can be deformed (straightened) under the influence of external forces, such as pulling opposite ends of the NG tube, but resiliently return to their original normally-bent shape when the external forces are removed. Similarly, the terms "normally-curved" and "normally-bent" are used herein to describe portions of the NG tube which can be deformed (straightened) by externally-applied forces (such as tension or radial constriction applied, for example, by the nasal passage or esophagus of a patient), but when such external forces are removed, the normally-curved or normally-bent portions of the NG tube resiliently return to their original curved/bent shape.

The normal curves and bends described below with respect to the first and second aspects of the present invention were created by the present inventor by heat treating a known NG tube. Specifically, the present inventor created the normal curves/bends in a known NG tube by inserting the known NG tube in boiling water, bending the NG tube into the desired shape, and cooling the tube in a common freezer. However, it should be recognized that these curves/bends may be formed using other methods known to those skilled in the art of manufacturing NG tubes.

First Embodiment (FIGS. 3(a) and 3(b))

FIG. 3(a) and FIG. 3(b) show side and top views of a NG tube 300 according to a first embodiment which incorporates the first, second and third aspects of the present invention.

Referring to FIGS. 3(a) and 3(b), the NG tube 300 is formed from a 3 to 4 foot length of stiff (but not rigid) plastic tubing 310 having a diameter D of 2 to 10 mm. One end of the tubing 310 is tapered and rounded to form a tip 320. In addition, the tubing 310 defines several openings 330 located near the tip 320 through which fluids may enter or leave one or more passages formed within the tubing 310.

In accordance with the first aspect of the present invention, the NG tube 300 includes a normally-bent portion 340 which separates a substantially-straight leading portion 350 and a subsequent (remaining) portion 360 of the tubing 310.

The normally-bent portion 340 is defined by an angle $\alpha$ formed at an intersection between a longitudinal axis 370a of the leading portion 350 and a longitudinal axis 370b of the subsequent portion 360. The angle $\alpha$ is preferably within the range of 10° to 65°. If the angle $\alpha$ is less than 10°, the pressure exerted by the tip 320 against a patient's nasopharynx becomes too great and increases patient discomfort. When the angle $\alpha$ is greater than 65°, the bent portion 340 can apply an undesirable amount of pressure against the walls of the nasal passage during insertion. The angle $\alpha$ is even more preferably within the range of 25° and 35°. The present inventor has determined that when the normally-bent portion 340 has this preferred angular range, the NG tube 300 is passed with a minimum amount of discomfort to the patient.

The leading portion 350 preferably has a length in the range of 0.5 to 2.0 inches, this length preferably being determined by the angle $\alpha$. In particular, if the angle $\alpha$ is greater (closer to 65°), the length of the leading portion 350 should be approximately 0.5 inches. Conversely, as the angle $\alpha$ flattens out, the length of the leading portion 350 may be increased. When the angle $\alpha$ is within the more preferred range of 25° to 35°, the preferred length of the leading portion 350 is approximately one inch.

In accordance with the second aspect of the present invention, an optional curved portion 380 may be formed immediately after the subsequent portion 360 (approximately 2 to 3 inches after the bend 340). The curved portion 380 is preferably 4 to 6 inches in length and has an arc radius of 2 to 4 inches. As discussed below, the curved portion 380 guides the tip 320 into the esophagus.

In accordance with the third aspect of the present invention, the NG tube 300 includes a longitudinal line or stripe formed on an outer surface of the flexible tubing to prompt the administering nurse/physician regarding the proper orientation of the NG tube 300 during insertion. The longitudinal line or stripe includes a first section 390a having a first end located adjacent the tip 320 and a second end located 4 to 7 inches from the closed end (near or in the second curved portion 380). The first section 390a is positioned along a convex (upwardly-bent) portion of the bent portion 340 (i.e., along the upper edge of the NG tube as viewed in FIG. 3(a)). A spiral or helical second section 390b extends from the second end of the first section 390a and wraps 180° around the circumference of the tubing 310 to an end point 390c which is located on the bottom edge of the NG tube (when viewed in FIG. 3(a))—that is, the end point 390c is located on the concave side of the bent portion 380. A straight third section 390d then extends from the end point 390c along the bottom edge of the NG tube. A spiral or helical fourth section 390e, which is located 10 to 16 inches from the tip 320, is connected to an end of the third section 390d and wraps 90° around the circumference of the tubing 310 to an end point 390e which is located on a side edge of the NG tube (when viewed in FIG. 3(b)). Finally, a straight fifth section 390f extends along the side edge of the NG tube from an end of the fourth section 390e. As discussed below, the various sections of the longitudinal line 390 prompt the administering nurse/physician as to the proper orientation and proper method for passing the NG tube 300 into a patient.

Second Embodiment (FIGS. 4(a) and 4(b))

FIG. 4(a) and FIG. 4(b) show side and top views of a NG tube 400 according to a second (and presently-preferred) embodiment which incorporates the first, second and third aspects of the present invention. In the following discussion, details regarding features which are common to both the NG tube 300 (discussed above) and the NG tube 400 are omitted for brevity.

Referring to FIGS. 4(a) and 4(b), the NG tube 400 is formed from a plastic tubing 410 having a tip 420 and defining several openings 430 located near the tip 420.

In accordance with the second aspect of the present invention, the NG tube 400 includes a normally-curved portion 440 located between the tip 420 and a subsequent (remaining) portion of the tubing 410.

The normally-curved portion 440 is formed along an arc radius R which is in the range of 1 to 4 inches and a length of 2 to 4 inches (this length varies according to the size of the patient). As shown in FIG. 4(a), the total curvature of the normally-curved portion along a longitudinal axis 445 between an initial axis portion 445a and an axis portion 445b located at the tip 420 is identified by the angle $\theta$. The angle $\theta$ is preferably in the range of 20° to 90°, depending upon the length and radius of the normally-curved portion 440, and depending upon the stiffness of the NG tube 400. If the angle $\theta$ is less than 20°, the pressure against a patient's posterior nasopharynx becomes too great. If the angle $\theta$ is greater than 90°, it becomes difficult to direct the tip 420 of the NG tube 400 into the esophagus. Ideally, the arc radius R and the length of the normally-curved portion 440 approximates the curvature of the superior and posterior aspects of the soft palate of each patient. Thus, the normally-curved portion 440 approximates the human anatomy and is anatomically conforming.

The normally-curved portion 440 of the second embodiment differs from the normally-bent portion 340 of the first embodiment in that the normally-curved portion 440 is gradually bent, whereas the bend 340 is comparatively abrupt. Therefore, the normally-curved portion 440 is typically more flexible than the bend 340 because the force required to straighten the normally-curved portion 440 can be spread out over a larger area than the force required to straighten the bend 340. As such, the present inventor has determined that the normally-curved portion 440 is relatively more comfortable to pass than the bend 340, and the NG tube 440 is preferred over the NG tube 300.

In accordance with the second aspect of the present invention, an optional curved portion 450 may be formed approximately 2 to 3 inches after the normally-curved portion 440). The curved portion 450 is preferably 4 to 6 inches in length and has an arc radius of 2 to 4 inches.

In accordance with the third aspect of the present invention, the NG tube 400 includes a longitudinal line or stripe formed on an outer surface of the flexible tubing 310 to prompt the administering nurse/physician regarding the proper orientation of the NG tube 400 during insertion. The longitudinal line or stripe includes a first section 460a having a first end located adjacent the tip 420 and a second end located 4 to 8 inches from the tip 420 (near the beginning of the second curved portion 450). The first section 460a is positioned along a convex (upwardly-bent) portion of the normally-curved portion 440 (i.e., along the upper edge of the NG tube as viewed in FIG. 4(a)). A spiral or helical second section 460b extends from the second end of the first section 460a and wraps 180° around the circumference of the tubing 410 to an end point 460c which is located on the bottom edge of the NG tube (when viewed in FIG. 4(a))—that is, the end point 460c is located on the concave side of the normally-curved portion 450. A straight third section 460d then extends from the end point 460c along the bottom edge of the NG tube. A spiral or helical fourth section 460e, which is located 10 to 16 inches from the tip 420, is connected to an end of the third section 460d and wraps 90° around the circumference of the tubing 410 to an end point 460e which is located on a side edge of the NG tube (when viewed in FIG. 4(b)). Finally, a straight fifth section 460f extends along the side edge of the NG tube from an end of the fourth section 460e.

Method of Insertion (FIGS. 5(a) through 5(f))

FIGS. 5(a) through 5(f) show procedural steps for inserting (passing) an NG tube having a normal curve or bend in accordance with the present invention.

The following discussion generally applies to both the NG tube 300 and the NG tube 400 of above-described first and second embodiments, as shown in FIGS. 3(a), 3(b), 4(a) and 4(b).

Figure 5A:
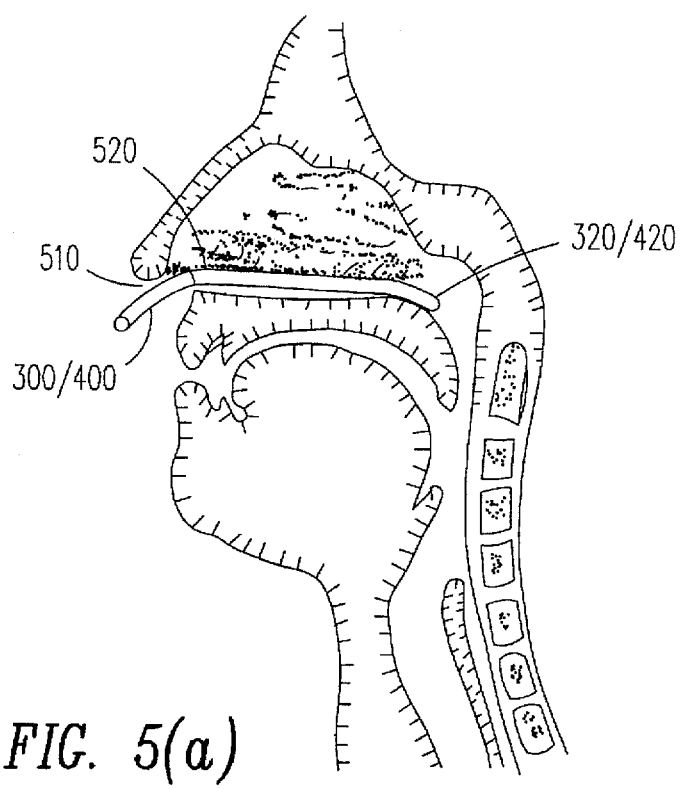
FIGS. 5(a) through 5(f) show procedural steps by which the nasogastric tubes of the first and second embodiments are passed into a patient in accordance with the present invention.

Referring to FIG. 5(a), the administering nurse/physician removes the NG tube 300/400 from the package and the tip 320/420 of the tube is lubricated with a water-soluble jelly. With the patient sitting, the tip 320/420 is inserted into the nostril 510, with the longitudinal line 390/460 (see FIGS. 3(a), 3(b), 4(a) and 4(b)) facing upward (superior), and advanced into the nasal passage 520. In this orientation, the concave side of the normally-curved or bent portion 340/440 faces downward (inferior) relative to patient's head. As shown, the nasal passage 520 applies radial pressure against the NG tube 300/400 which tends to straighten (flatten) the normally-curved or bent portion 340/440.

Figure 5B:
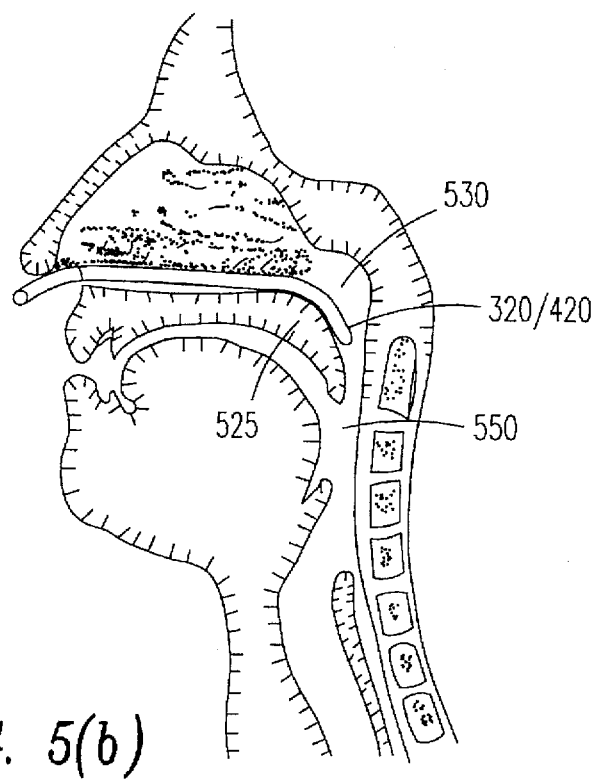
Figure 5C:
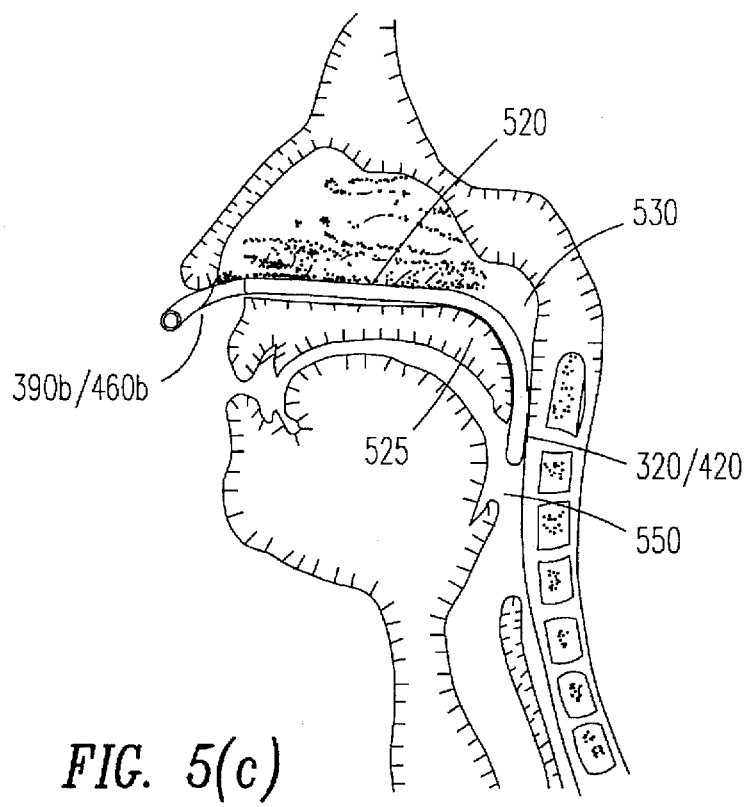

As shown in FIGS. 5(b) and 5(c), the tip 320/420 passes over the superior and posterior surface of the soft palate turning inferior into the oropharynx 550. The radial pressure applied by the nasal passage 520 is released from the NG tube 300/400. As the radial pressure is released, the normally-curved or bent portion 340/440 resiliently returns to its original shape, thereby turning the tip 320/420 inferior toward the oropharynx 550. Because the tip 320/420 is turned inferior, the NG tube 300/400 more easily negotiates the bend into the oropharynx 550, thereby reducing the discomfort caused during insertion of known NG tubes. Further, the NG tube 400 of the second embodiment provides an additional level of comfort for the patient in that the tip 420 applies reduced pressure against the posterior nasopharynx due to its normally-curved shape (which approximates the superior and posterior surface of the soft palate 525).

Figure 5D:
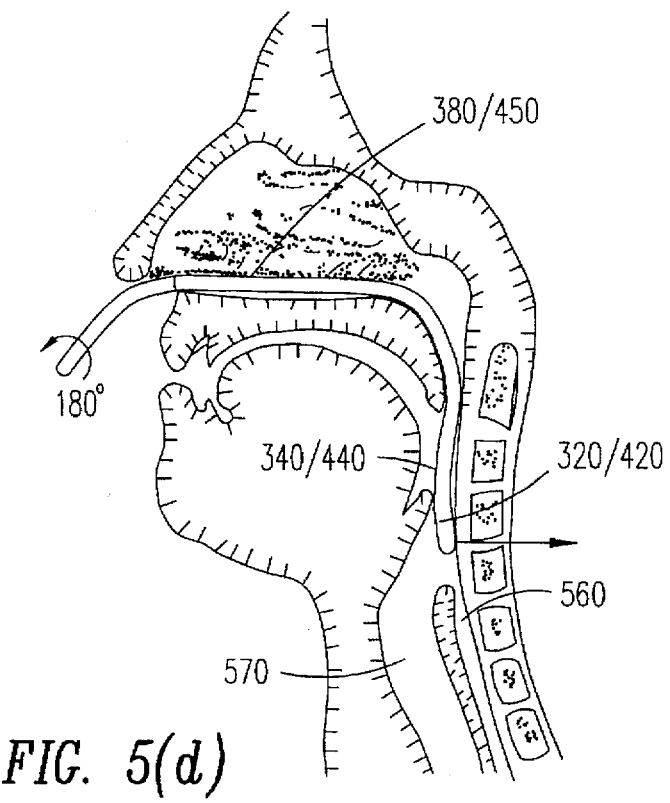

Referring to FIG. 5(d), when the tip 320/420 enters the oropharynx, the second section 390b/460b of the line or stripe of the NG tube 300/400 enters the patient's nostril 510. At this time, the administering nurse/physician rotates the tube 180° in a counter-clockwise direction, thereby maintaining the upward (superior) orientation of the second section 390b/460b. This 180° rotation turns the tube such that the tip 320/420 is biased by the normally-curved or bent portion 340/440 in a posterior direction (i.e., toward the patient's spine). This positions the tip 320/420 in a proper orientation for insertion into the esophagus 560, and away from the voice box 570, thereby facilitating easier and more reliable passing of the tube.

Figure 5E:
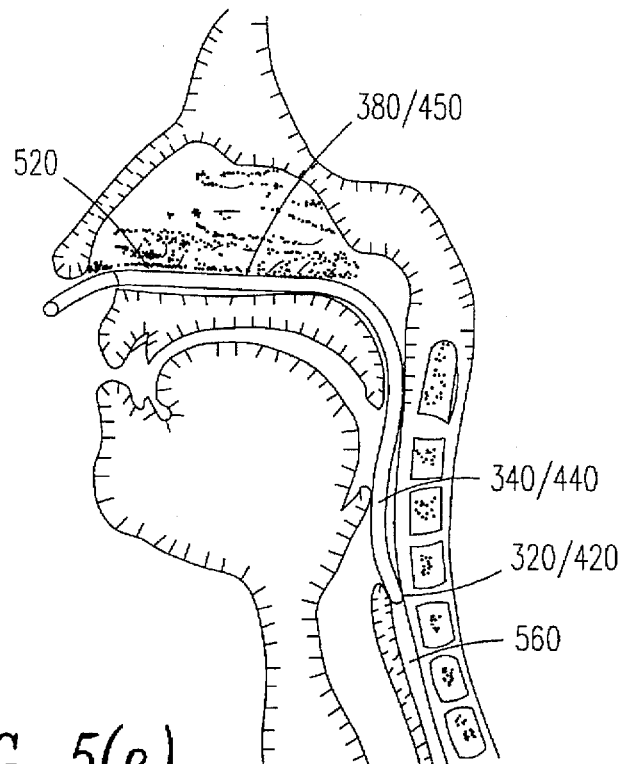

As shown in FIGS. 5(d) and 5(e), as the tip 320/420 is advanced toward and into the esophagus 560, the second curved portion 380/450 enters the nasal passage 520 and produces an additional bending force on the tube, thereby more reliably forcing the tip 320/420 in the posterior direction.

Figure 5F:
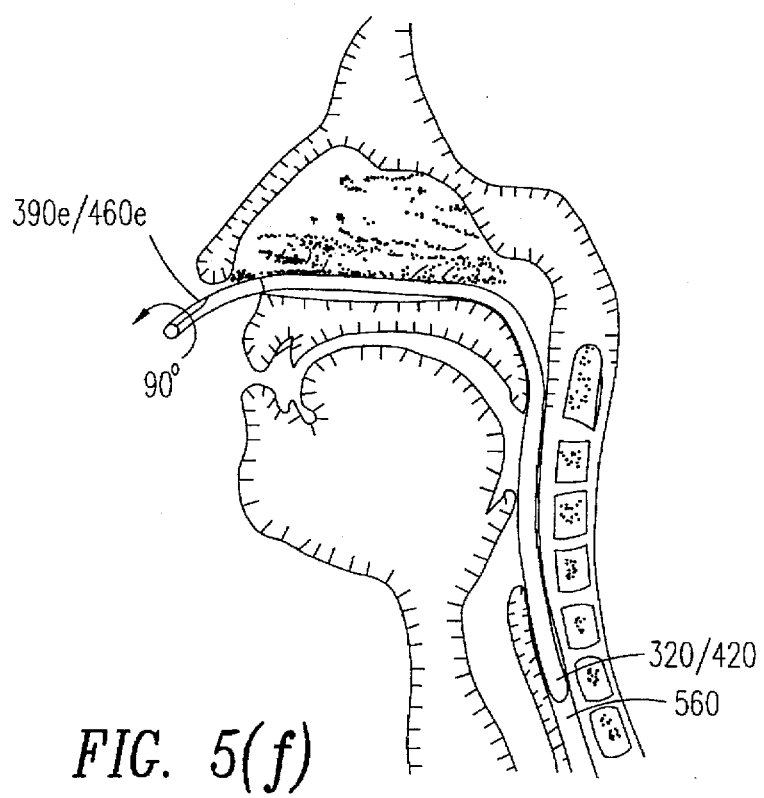

As shown in FIG. 5(f), after the tip 320/420 has entered the esophagus 560, the curved line section 390e/460e reaches the patient's nostril 510, thereby prompting the administering nurse/physician to turn the NG tube 300/400 90° in a counter-clockwise direction. This 90° rotation orients the tip 320/420 toward the patient's right side, thereby directing the tip 320/420 toward the outlet area of the patient's stomach (not shown).

When the tube is advanced into the stomach, placement is verified by pushing air into the tube while listening over the stomach. Appropriate gurgling should be heard. The tube is then aspirated with a syringe, again verifying proper placement. The tube is secured in a manner known in the art.

With the above-described procedure, an NG tube can be passed through the patient's nasopharynx with a reduced amount of discomfort, thereby making the passing procedure as pleasant as possible for the patient and reducing the risk of the potentially dangerous complications produced when the known NG tube is pushed against the posterior nasopharynx. In addition, the procedure allows for more reliable passage of the tip into the esophagus, thereby reducing the risk of complications produced when the tip is inadvertently passed into the trachea. Finally, the procedure more reliably positions the tip in the outlet of the patient's stomach, thereby making the procedure less time-consuming and reducing the need for radiographic verification of proper placement.

While particular embodiments of the present invention have been shown and described, it will be obvious to those skilled in the art that changes and modifications may be made without departing from this invention in its broader aspects. For example, the tube may be bent or curved into shapes outside of the suggested ranges discussed above, although such shapes would produce greater discomfort to the patient. In addition, the longitudinal line or stripe may be replaced with a marking system wherein three different colors, for example red, white and blue, are alternately applied to the tube indicating where the tube is to be rotated, or otherwise providing instructions to the administering nurse/physician during insertion. Also, the second rotation (90°) could be eliminated if specific positioning in the stomach is not required. If this be the case, the first rotation (180°) could be clockwise rather than counter-clockwise. This change from a counter-clockwise to a clockwise rotation might be preferred by some physicians or nurses. Therefore, the appended claims are intended to encompass within their scope all such changes and modifications which fall within the true spirit and scope of this invention.

We claim:

1. A nasogastric tube for insertion through a patient's nasal passage and esophagus, the nasogastric tube comprising a flexible tubing having a closed end, the flexible tubing including a normally-bent portion which is located between a leading portion of the flexible tubing, which is located adjacent the closed end, a subsequent portion of the flexible tubing attacked to the normally-bent portion, and a normally-curved portion located 2 to 3 inches from the normally-bent portion;

wherein the normally-bent portion forms an angle which is in the range of 10° to 65° with respect to a longitudinal axis of the subsequent portion of the flexible tubing;

wherein the leading portion of the tube is 0.5 to 2 inches in length; and wherein the normally-curved portion is 4 to 6 inches in length and has an arc radius of 2 to 4 inches.

2. The nasogastric tube according to claim 1, wherein the normally-bent portion forms an angle which is in the range of 25° to 35° with respect to the longitudinal axis of the subsequent portion of the flexible tubing.

3. The nasogastric tube according to claim 1, further comprising a longitudinal line formed on an outer surface of the flexible tubing, the longitudinal line including:

a first section having a first end located adjacent the closed end and a second end located 4 to 7 inches from the closed end, the first section extending along a convex portion of the normally-bent portion, a second section extending from the second end of the first section around the circumference of the tube to an end point which is located 180° from the second end of the first section, and a third section extending from the end point away from the normally-bent portion.

4. The nasogastric tube according to claim 3, wherein the third section includes an end which is 10 to 16 inches from the closed end, and the longitudinal line includes a fourth section extending from the end of the third section around the circumference of the tube to an end point which is located 90° from the end of the third section.

5. A nasogastric tube for insertion through a patient's nasal passage and esophagus, the nasogastric tube comprising a flexible tubing having a closed end, wherein a leading portion of the flexible tubing is located adjacent the closed end and includes a first normally-curved portion, the first normally-curved portion having an arc radius which is in the range of 1 to 4 inches and having a length which is less than or equal to 4 inches; and wherein a second normally-curved portion of the flexible tubing is located 2 to 3 inches from the first normally-curved portion, the second normally-curved portion being 4 to 6 inches in length and having an arc radius of 2 to 4 inches.

6. The nasogastric tube according to claim 5, further comprising a longitudinal line formed on an outer surface of the flexible tubing, the longitudinal line including:

a first section having a first end located adjacent the closed end and a second end located 4 to 7 inches from the closed end, the first section extending along a convex portion of the first normally-curved portion, a second section extending from the second end of the first section around the circumference of the tube to an end point which is located 180° from the second end of the first section, and a third section extending from the end point away from normally-curved portion of the tube.

7. The nasogastric tube according to claim 6, wherein the third section includes an end which is 12 to 16 inches from the closed end, and the longitudinal line includes a fourth section extending from the end of the third section around the circumference of the tube to an end point which is located 90° from the end of the third section.

8. A method for passing a nasogastric tube through a patient's nasal passage and into the patient's esophagus, the nasogastric tube being formed from flexible tubing and having a closed end and a first normally-curved portion located adjacent the closed end, the first normally-curved portion having an arc radius which is in the range of 1 to 4 inches, a length which is less than or equal to 4 inches, and a concave side, the nasogastric tube also having a second normally-curved portions which is located 2 to 3 inches from the first normally-curved portion, has a length of 4 to 6 inches, and has an arc radius of 2 to 4 inches, the method comprising:

inserting the nasogastric tube into a nostril of the patient such that the concave side of the first normally-curved portion faces inferior relative to the patient's head, whereby the first normally-curved portion is deformed from an original curved shape into a straightened shape as the first normally-curved portion passes through the patient's nasal passage, and whereby the first normally-curved portion is deformed from the straightened shape to the originally curved shape as the first normally-curved portion passes over the patient's soft palate, thereby directing the closed end inferior into the patient's oropharynx;

when the nasogastric tube has been inserted such that the closed end is located in the oropharynx of the patient, rotating the nasogastric tube such that the closed end is biased posteriorly by the first normally-curved portion toward the patient's spine;

further inserting the nasogastric tube such that the closed end is received into the patient's esophagus.

9. The method of claim 8, wherein the step of rotating the tube comprises rotating the tube 180°.

10. The method of claim 8, wherein the tube includes a longitudinal line formed on an outer surface of the flexible tubing, the longitudinal line including:

a first section having a first end located adjacent the closed end and a second end located 4 to 7 inches from the closed end, the first section extending along a convex portion of the first normally-curved portion, a second section extending from the second end of the first section around the circumference of the tube to an end point which is located 180° from the second end of the first section, and a third section extending from the end point away from the normally-curved portion of the tube;

and wherein the steps of inserting, rotating and further inserting the tube further comprise maintaining the nasogastric tube such that a portion of the longitudinal line located adjacent the patient's nostril faces superior.

11. The method of claim 8, wherein the step of further inserting the tube comprises:

pushing the tube until the closed end enters the patient's esophagus;

turning the tube 90° such that the curved tip faces a right side of the patient, and pushing the tube until the curved tip is received in the outlet of the stomach.

12. A method for passing a nasogastric tube through a patient's nasal passage and into the patient's esophagus, the nasogastric tube being formed from flexible tubing and having a closed end, a leading portion located adjacent the closed end, a normally-bent portion attached to the leading portion, and a subsequent portion extending from the normally-bent portion, the leading portion of the tube being 0.5 to 2 inches in length, the normally-bent portion forming an angle which is in the range of 10° to 65° with respect to a longitudinal axis of the subsequent portion of the flexible tubing and having a concave side, the nasogastric tube also having a normally-curved portion which is located 2 to 3 inches from the normally-bent portion, has a length of 4 to 6 inches, and has an arc radius of 2 to 4 inches, the method comprising:

inserting the nasogastric tube into a nostril of the patient such that the concave side of the normally-bent portion faces inferior relative to the patient's head, whereby the normally-bent portion is deformed from an original bent shape into a straightened shape as the normally-bent portion passes through the patient's nasal passage, and whereby the normally-bent portion is deformed from the straightened shape to the originally bent shape as the normally-bent portion passes over the patient's soft palate, thereby directing the closed end inferior into the patient's oropharynx;

when the nasogastric tube has been inserted such that the closed end is located in the oropharynx of the patient, rotating the nasogastric tube such than the closed end is biased posteriorly by the normally-bent portion toward the patient's spine;

further inserting the nasogastric tube such that the closed end is received into the patient's esophagus.

13. The method of claim 12, wherein the step of rotating the tube comprises rotating the tube 180°.

14. The method of claim 12, wherein the tube includes a longitudinal line formed on an outer surface of the flexible tubing, the longitudinal line including:

a first section having a first end located adjacent the closed end and a second end located 4 to 7 inches from the closed end, the first section extending along a convex portion of the first normally-bent portion, a second section extending from the second end of the first section around the circumference of the tube to an end point which is located 180° from the second end of the first section, and a third section extending from the end point away from the normally-bent portion of the tube;

and wherein the steps of inserting, rotating and further inserting the tube further comprise maintaining the nasogastric tube such that a portion of the longitudinal line located adjacent the patient's nostril faces superior.

15. The method of claim 12, wherein the step of further inserting the tube comprises:

pushing the tube until the closed end enters the patient's esophagus;

turning the tube 90° such that the curved tip faces a right side of the patient, and pushing the tube until the curved tip is received in the outlet of the stomach.

* * * * *